US007759081B2

(12) United States Patent
Hanash et al.

(10) Patent No.: US 7,759,081 B2
(45) Date of Patent: Jul. 20, 2010

(54) ANNEXIN PROTEINS AND AUTOANTIBODIES AS SERUM MARKERS FOR CANCER

(75) Inventors: Samir M. Hanash, Ann Arbor, MI (US); David Misek, Ann Arbor, MI (US); Robert Hinderer, Flint, MI (US); David Beer, Chelsea, MI (US); Franck Brichory, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 588 days.

(21) Appl. No.: 11/425,528

(22) Filed: Jun. 21, 2006

(65) Prior Publication Data

US 2007/0037227 A1 Feb. 15, 2007

Related U.S. Application Data

(62) Division of application No. 10/656,356, filed on Sep. 5, 2003, now abandoned, which is a division of application No. 09/370,337, filed on Aug. 6, 1999, now Pat. No. 6,645,465.

(51) Int. Cl.
*G01N 33/574* (2006.01)
(52) U.S. Cl. .......................................... 435/8; 435/7.23
(58) Field of Classification Search ................. 435/7.23, 435/8
See application file for complete search history.

(56) References Cited

U.S. PATENT DOCUMENTS

| 5,316,915 A | 5/1994 | Kraus et al. | 435/7.95 |
| 5,405,749 A | 4/1995 | Polans et al. | 435/7.23 |
| 5,741,654 A | 4/1998 | Michel et al. | 435/7.9 |

FOREIGN PATENT DOCUMENTS

| JP | 07072149 | * | 3/1995 |
| WO | 9900671 | | 1/1999 |
| WO | 0039557 | | 7/2000 |

OTHER PUBLICATIONS

Traverso et al. (Journal of Cell Science 1998; 111: 1405-1418).*
Slamon et al. (Science vol. 235, Jan. 1987, pp. 177-182).*
Soussi, "The humoral response to the tumor-suppressor gene product p53 in human cancer: implications for diagnosis and therapy", Immunol. Today, vol. 17, No. 8, pp. 354-356.
Miyachi et al., "Autoantibody to a Nuclear Antigen in Proliferating Cells", vol. 121, No. 6, Dec. 1978, pp. 2228-2234.
Bachvaroff et al., "Appearance of cytoskeletal components on the surface of leukemia cells and oflymphocytes transformed by mitogens and Epstein-Barr virus", Proc. Natl. Acad. Sci. USA, vol. 77, No. 8, Aug. 1980, pp. 4979-4983.
Crawford et al., "Detection of Antibodies Against the Cellular Protein p53 In Sera from Patients with Breast Cancer", Int. J. Cancer 30, 1982, pp. 403-408.
Wallner et al., "Cloning and expression of human lipocortin, a phospholipase A.sub.2 inhibitor with potential anti-inflammatory activity", Nature, vol. 320, Mar. 1986, pp. 77-80.
Weber et al., "Repeating sequence homologies in the p36 target protein of retroviral protein kinses and lipocortin, the p37 inhibitor of phospholipase A.sub.2", FEBS Letters, vol. 203, No. 1, Jul. 1986, pp. 95-98.
Saris et al, "The cDNA Sequence for the Protein-Tyrosine Kinase Substrate p36 (Calpactin 1 Heavy Chain) Reveals a Multidomain Protein with Internal Repeats", Cell, vol. 46, Jul. 18, 1986, pp. 201-212.
Huang et al., "Two Human 35 kd Inhibitors of Phospholipase A.sub.2 Are Related to Substrates of pp60.sup.v-src and of the Epidermal Growth Factor Receptor/Kinase", Cell, vol. 46, Jul. 18, 1986, pp. 191-199.
Tan et al., "PCNA/Cyclin: A Lupus Antigen Connected with DNA Replication", J. Rheumatol., Supp. 13, vol. 14, 1987, pp. 89-96.
William et al., "Differentiation of HL-60 Cells is Associated with an Increase in the 35-KDa Protein Lipocortin I", 1988, J. Cellular Physiology 137: 402-410.
Ben-Mahrez et al., "Circulating Antibodies Against C-MYC Oncogene Product in Sera of Colorectal Cancer Patients", Int. J. Cancer 46, 1990, pp. 35-38.
Sorokine et al., "Presence of Circulating Anti-c-myp Oncogene Product Antibodies in Human Sera", Int. J. Cancer: 47, 1991, pp. 665-669.
Tockman et al., *Cancer Res.*, 1992, 52:2711s-2718s.
Kraus et al., *Jnl. of Immunoassay*, v13 (3), 1992, pp. 411-439.
Bandorowicz et al., "Annexins—multifunctional, calcium-dependent phosphloipid-binding proteins", Acta Biochimica Polonica, vol. 40, No. 3, 1993, pp. 281-293.
Pupa et al., "Antibody response against the c-*erb*B-2 oncoprotein in breast carcinoma patients", 1993, Cancer Research 53: 5864-5866.
Bastian et al., "Autoantibodies to annexins: a diagnostic marker for cutaneous disorders?", 1994, Journal of Dermatological Science 8: 194-202.

(Continued)

*Primary Examiner*—Brandon J Fetterolf
(74) *Attorney, Agent, or Firm*—Arent Fox LLP

(57) ABSTRACT

The present invention relates to screening methods for diagnosis, prognosis, or susceptibility to cancer in a subject by means of detecting the presence of serum autoantibodies to specific annexin protein antigens in sera from subjects. The present invention also provides screening methods for diagnosis and prognosis of cancer in a subject by means of detecting increased expression levels of annexin proteins in biological samples of the subject. The method of the invention can also be used to identify subjects at risk for developing cancer. The method of the invention involves the use of subject derived biological samples to determine the occurrence and level of expression of annexin proteins or expression of annexin derived peptides or antigens, and/or the occurrence and level of circulating autoantibodies to specific annexin protein antigens. The present invention further provides for kits for carrying out the above described screening methods. Such kits can be used to screen subjects for increased levels of annexin proteins, or for the detection of autoantibodies to annexin proteins, as a diagnostic, predictive or prognostic indicator of cancer.

4 Claims, 9 Drawing Sheets

OTHER PUBLICATIONS

Figure 1:
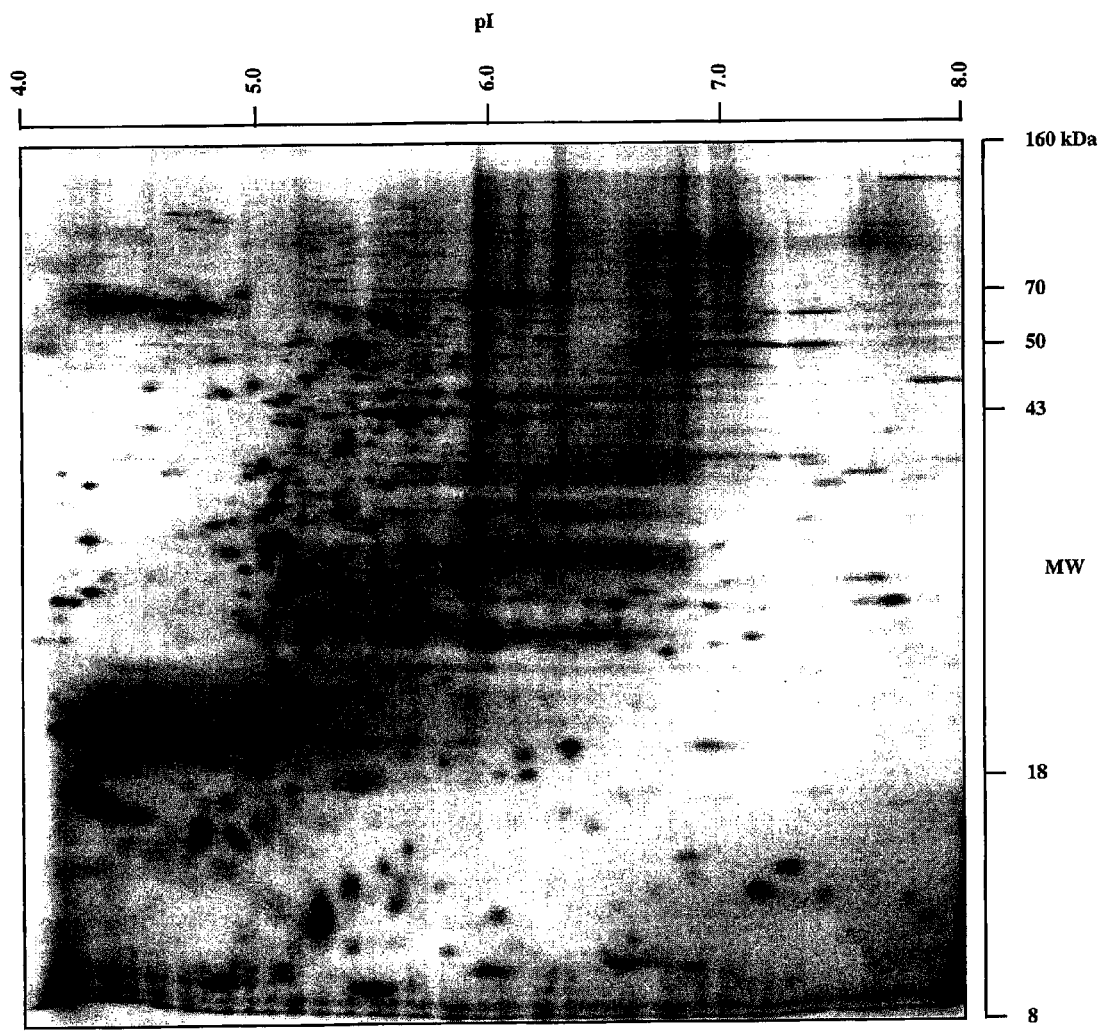

Swairjo et al., "Annexin Structure and Mebrance Interactions: A Molecular Perspective", Annu. Rev. Biophys. Biomol. Struct. 23, 1994, pp. 193-213.

Mao et al., "Detection of Oncogene Mutations in Sputum Precedes Diagnosis of Lung Cancer", Cancer Res. 54, Apr. 1, 1994, pp. 1634-1637.

Davis et al., "Detection of Secreted and Intracellular Annexin II by a Radiommunoassay", 1995, Journal of Immunological Methods 188: 91-95.

Liemann et al., "Annexins: a novel family of calcium- and membrane-binding proteins in search of a function", Structure, vol. 3, No. 3, 1995, pp. 233-237.

Gourevitch et al., "Polymorphic epithelial mucin (MUC-1)-containing circulating immune complexes in carcinoma patietns", Br. J. Cancer 72, 1995, pp. 934-938.

Tsao et al., "Annexin I in Female Rabbit Reproductive Organs: Varying Levels in Relation to Maturity and Pregnancy", 1995, Lipids 30: 507-511.

Peyrate et al., "Prognostic significance of circulating P53 antibodies in patients undergoing surgery for locoregional breast cancer", Lancet, vol. 345, Mar. 1, 1995, pp. 621-622.

Lubin et al., "Serum p53 antibodies as early markers of lung cancer", Nat. Med., vol. 1, No. 7, Jul. 1995, pp. 701-702.

Mills et al., "Detection of K-ras Oncogene Mutations in Bronchoalveolar Lavage Fluid for Lung Cancer Diagnosis", J. Natl. Cancer Inst., vol. 87, No. 14, Jul. 19, 1995, pp. 1056-1060.

Takahashi et al., "Antibody to ras Proteins in Patients with Colon Cancer", Clin. Cancer Res., vol. 1, Oct. 1995, pp. 1071-1077.

Travis et al., "United States Lung Carcinoma Incidence Trends", Cancer, vol. 77, No. 12, Jun. 15, 1996, pp. 2464-2470.

Yamamoto et al., "Detection of auto-antibodies against L-myc Oncogene Products in Sera From Lung Cancer Patients", J. Int. Cancer (Pred. Oncol) 69, 1996, pp. 283-289.

Gerke et al., "Annexins and membrane dynamics", Biochemica et Biophysica Acta 1357, 1997, pp. 129-.

Donnelly et al., "Annexins in the secretory pathway", Cell Mol. Life Sci. 53, 1997, pp. 533-538.

Mollenhuaer, "Annexins: what are they good for?", Cell Mol. Life Sci. 53, 1997, pp. 506-507.

Gao et al., "Distribution of p53 and K-ras mutations in human lung cancer tissues", Carcinogenesis, vol. 18, No. 3, 1997, pp. 473-478.

Benz et al., "Annexins: From Structure to Function", Biol. Chem., vol. 378, Mar./Apr. 1997, pp. 177-183.

Iizasa et al., "Serum anti-p53 autoantibodies in primary resected non-small-cell lung carcinoma", Cancer Immunol. Immunother. 46, 1998, pp. 345-349.

Stockert et al., "A survey of the humoral ammune response of cancer patients to a panel of human tumor antigens", J. Exp. Med. 187, 1998, pp. 1349-1354.

Cawley et al., "Anti-p53 Antibodies in Patients with Barrett's Esophagus or Esophagael Carcinoma Can Predate Cancer Diagnosis", Gastroenterology, vol. 115, No. 1, 1998, pp. 19-27.

Pencil et al., "Elevated Levels of Annexin I Protein in Vitro and In Vivo in Rat and Human Mammary Adenocarcinoma", 1998, Clin. Exp. Metastasis 16:113-121.

Gure et al., "Human Lung Cancer Antigens Recognized by Autologous Antibodies: Definition of a Novel cDNA Derived from the Tumor Suppressor Gene Locus on Chromosome 3p21.3", Cancer Res. 58, Mar. 1, 1998, pp. 1034-1041.

Old et al., "New Paths in Human Cancer Serology", J.Exp. Med., vol. 187, No. 8, Apr. 20, 1998, pp. 1163-1167.

Brichory et al., An immune response manifested by the common occurrence of annexins I and II autoantibodies and high circulating levels of IL-6 in lung cancer. *PNAS*, vol. 99 No. 17, Aug. 14, 2003.

Cervical cancer vaccine success, *BBC News*, Mar. 14, 2006 16:11.

* cited by examiner

ANNEXIN PROTEINS AND AUTOANTIBODIES AS SERUM MARKERS FOR CANCER

CROSS REFERENCE TO RELATED APPLICATION

The present application is a divisional of U.S. patent application Ser. No. 10/656,356 filed Sep. 5, 2003, now abandoned, which is a divisional of U.S. patent application Ser. No. 09/370,337, filed Aug. 6, 1999, now U.S. Pat. No. 6,645,465 B2, entitled ANNEXIN PROTEINS AND AUTOANTIBODIES AS SERUM MARKERS FOR CANCER.

1. INTRODUCTION

The present invention relates to screening methods for diagnosis, prognosis, or susceptibility to cancer in a subject by means of detecting the presence of serum autoantibodies to specific annexin protein antigens in sera from subjects. The present invention also provides screening methods for diagnosis and prognosis of cancer in a subject by means of detecting increased expression levels of annexin proteins in biological samples of the subject. The method of the invention can also be used to identify subjects at risk for developing cancer. The method of the invention involves the use of subject derived biological samples to determine the occurrence and level of expression of annexin proteins or expression of annexin derived peptides or antigens, and/or the occurrence and level of circulating autoantibodies to specific annexin protein antigens. The present invention further provides for kits for carrying out the above described screening methods. Such kits can be used to screen subjects for increased levels of annexin proteins, or for the detection of autoantibodies to annexin proteins, as a diagnostic, predictive or prognostic indicator of cancer. The invention is demonstrated by way of examples in which elevated levels of annexin proteins, and elevated levels of circulating autoantibodies reactive against annexin proteins, have been observed in the sera of cancer subjects.

2. BACKGROUND OF THE INVENTION

A number of cellular proteins have been demonstrated to occur at increased levels in body fluids of subjects with different types of cancer. The increased levels of such proteins in cancer subjects provide diagnostic and prognostic assays for the presence of cancer. For example, elevated serum levels of prostate specific antigen (PSA) is frequently used as an indicator of the presence of prostate cancer in men.

Autoantibodies to normal or modified cellular proteins are known to be produced by patients in certain diseases such as autoimmune diseases and cardiovascular-related disorders, in some cases even before the disease has produced overt symptoms. There is also increasing evidence for a humoral immune response to cancer in humans, as demonstrated by the identification of antibodies against a number of intracellular and surface antigens in patients with various tumors (Gourevitch et al., 1995, Br. J. Cancer 72:934-938; Yamamoto et al., 1996, Int. J. Cancer, 69:283-289; Stockert et al., 1998, J. Exp. Med. 187:1349-1354; Gure et al., 1998, Cancer Res. 58:1034-1041). For example, somatic alterations in the p53 gene elicit a humoral response in 30-40% affected patients (Soussi, 1996, Immunol. Today 17:354-356). In some instances, the detection of anti-p53 antibodies can predate the diagnosis of cancer (Lubin et al., 1995, Nat. Med. 7:701-702; Cawley et al., 1998, Gastroenterology 115:19-27). U.S. Pat. No. 5,405,749 discloses a method of screening for cancer-associated retinopathy autoantigen and testing a patient's serum for autoantibody to the autoantigen. In addition, increases in relative rates of synthesis of major cytoskeletal proteins have been observed on the surface of leukemic cells and of lymphocytes transformed by mitogens and Epstein-Barr Virus (Bachvaroff, R. J. et al., 1980, Proc. Natl Acad. Sci. 77:4979-4983).

The majority of tumor derived antigens that have been identified and that elicit a humoral response are not the products of mutated genes. They include differentiation antigens and other gene products that are overexpressed in tumors (Old and Chen, 1998, J. Exp. Med. 187: 1163-1167). It is not clear why only a subset of patients with a tumor type develop a humoral response to a particular antigen. Factors that influence the immune response may include variability among individuals in major histocompatibility complex molecules. It is also possible that proteins may become immunogenic after undergoing a post-translational modification, a process which may be variable among tumors of a similar type.

Lung cancer is the most common cancer in the United States and accounts for over one fourth (28%) of cancer deaths in the US (Travis et al., 1996, Cancer 77:2464-2470). A number of molecular alterations including c-myc amplification, Ki-ras or p53 mutations have been identified that may affect tumor behavior (Mao et al., 1994, Cancer Res 54:1634-1637, Mills et al., 1995, J. Natl. Cancer Inst. 87:1056-1060, Gao et al., 1997, Carcinogenesis 18:473-478). Serum autoantibodies against the product oncogenes and tumor suppressor genes, such as c-myc (Ben-Mahrez et al., 1990, Int. J. Cancer 46:35-38), c-myb (Sorokine et al., 1991, Int. J. Cancer 47:665-669), c-erbB-2 (Pupa et al., 1993, Cancer Res 53:5864-5866), ras (Takahashi et al., 1995, Clin. Cancer 1:107) and p53 (Peyrat et al., 1995, Lancet 345:621-622; Iizasa et al., 1998, Cancer Immunol. Immunother. 46:345-349), have been reported in patients with various malignant diseases. Autoantibodies against L-myc oncogene products have been reported in 10% of sera from patients with lung cancer (Yamamoto et al., 1996, Int. J. Cancer 69:283-289). Serum autoantibodies against p53 have also been detected in sera of non-small-cell lung cancer patients (NSCLC) (Iizasa et al., 1998, Cancer Immunol. Immunother. 46:345-349). Elevated serum titers of anti-p53 autoantibodies were present in approximately 20% of the cases of (NSCLC), and the occurrence of these autoantibodies reflect the presence of p53 mutations and p53 over expression (Yamamoto et al., 1996, Int. J. Cancer 69:283-289).

The detection of autoantibodies to cellular antigens and the identification of proteins that have elicited autoantibodies has been accomplished using a variety of approaches. For example, Proliferating Cell Nuclear Antigen (PCNA) was first described as a nuclear antigen which bound antibodies from some patients with lupus erythematosus (Miyachi, K., Fritzler, M. J., and Tan, E. M., 1978, J. Immunol 121:2228-2234). It was subsequently observed that resting lymphocytes did not react with the antibody, in contrast to mitogen stimulated lymphocytes which displayed nuclear staining. This ultimately led to the identification of the protein, designated PCNA which is recognized by this autoantibody in lupus (Tan, E. M., Ogata, K., and Takasaki, Y., 1987, J. Rheumatol., 13:89-96). In some other cases, candidate proteins are singled out and investigated with respect to their ability to induce antibodies in patients, as was investigated for p53 (Crawford, L. V., Firm, D. C., Bulbrook, R. D., 1984, Int J Cancer 30:403-408). In addition, a technique called SEREX relies on serological analysis of recombinant cDNA expression libraries to identify tumor antigens (Old, L., et al. 1998, J. Exp. Med.

187:1163-1167). Thus, many approaches have been followed to search for proteins against which autoantibodies may be produced.

Annexins are a family of calcium-dependent phospholipid-binding proteins that are expressed ubiquitously in different tissues and cell types of higher and lower eukaryotes (Benz, J. and Hofmann, A., 1997, Biol. Chem 378:177-183). At least twelve annexin proteins have been identified. Among the many roles suggested for the annexin family of proteins, those implicating the proteins in regulated exocytosis remain the most convincing (Donnelly, S R and Moss S E, Cell., 1997, Mol. Life Sci. 53:533-538). A typical annexin protein is characterized by two distinct features, (i) $Ca^{2+}$-dependent binding to phospholipids; and (ii) the presence of a conserved sequence element of about 70 amino acids which is repeated four or eight times in a given member of the family. Immunocytochemical studies of annexins have shown that they reside subadjacent to plasma membranes, near calcium-sequestering intracellular organelles (Gerke, V and Moss, S E, 1997, Biochimica et Biophysica Acta 1357:129-154). Physical properties associated with annexins include inhibition of phospholipase $A_2$, anticoagulant activity, binding to cytoskeletal proteins, aggregation of membranes and vesicles and calcium-selective channel activity. Increased levels of annexin have been found to be associated with a number of diseases including multiple sclerosis and experimental neuritis.

3. SUMMARY OF THE INVENTION

It is an object of the present invention to provide screening methods for the diagnostic and prognostic evaluation of cancer, for the identification of subjects possessing a predisposition to cancer, and for monitoring patients undergoing treatment of cancer, based on the detection of elevated levels of annexin autoantibodies in biological samples of subjects. The invention also provides methods for detecting overproduction of annexin proteins and/or overproduction of groups of annexin proteins as a diagnostic or prognostic indicator of cancer.

The present invention relates to diagnostic evaluation and prognosis of cancer by detecting autoantibodies to annexin protein antigens in the serum of subjects with cancer or with precancerous lesions. The detection of increased serum levels of autoantibodies to annexin proteins constitutes a novel strategy for screening, diagnosis and prognosis of cancer.

The present invention provides for the use of the annexin protein antigens in immunoassays designed to detect the presence of serum autoantibodies to the annexin protein antigens. Such immunoassays can be utilized for diagnosis and prognosis of cancer. In accordance with the invention, measurement of annexin autoantibody levels in a subject's serum can be used for the early diagnosis of cancer. Moreover, the monitoring of serum autoantibody levels can be used prognostically to stage progression of the disease.

The invention further relates to assays developed to detect the level of annexin proteins in a subject's sample. Such assays include immunoassays wherein the annexin proteins are detected by their interaction with anti-annexin specific antibodies. For example, annexin antibodies or fragments of antibodies may be used to quantitatively detect the presence and amount of annexin proteins in a subject's sample.

The invention also relates to the use of annexin proteins as antigens to immunize patients suffering from diseases characterized by increased expression levels of the annexin protein antigens. Stimulation of an immunological response to such antigens, is intended to elicit a more effective attack on tumor cells; such as inter alia inhibiting tumor cell growth or facilitating the killing of tumor cells. The identification of autoantibodies to annexin protein antigens associated with particular cancers provides a basis for immunotherapy of the disease.

The invention further provides for pre-packaged diagnostic kits which can be conveniently used in clinical settings to diagnose patients having cancer or a predisposition to developing cancer. The kits can also be utilized to monitor the efficiency of agents used for treatment of cancer. In one embodiment of the invention, the kit comprises components for detecting and/or measuring the levels of autoantibodies directed toward annexin antigens in a sample. In a second embodiment, the kit of the invention comprises components which detect and/or measure annexin antigens in the biological sample.

The present invention is based on the discovery that expression levels of Annexin I and II are increased in tumor tissue samples derived from subjects with pulmonary adenocarcinoma or squamous cell lung cancer. Additionally, increased levels of autoantibodies against Annexin I and II were detected in the serum of the subjects with lung adenocarcinoma and squamous cell carcinoma. The finding that levels of annexin proteins and annexin autoantibodies are increased in samples derived from cancer subjects provides a basis for development of diagnostic and prognostic methods as well as a means for monitoring the efficacy of various therapeutic treatments for cancer.

4. BRIEF DESCRIPTION OF THE DRAWINGS

FIG. 1. Two-dimensional gel electrophoresis of A549 cell lysates. The gel was stained with silver to visualize the proteins.

Figure 2:
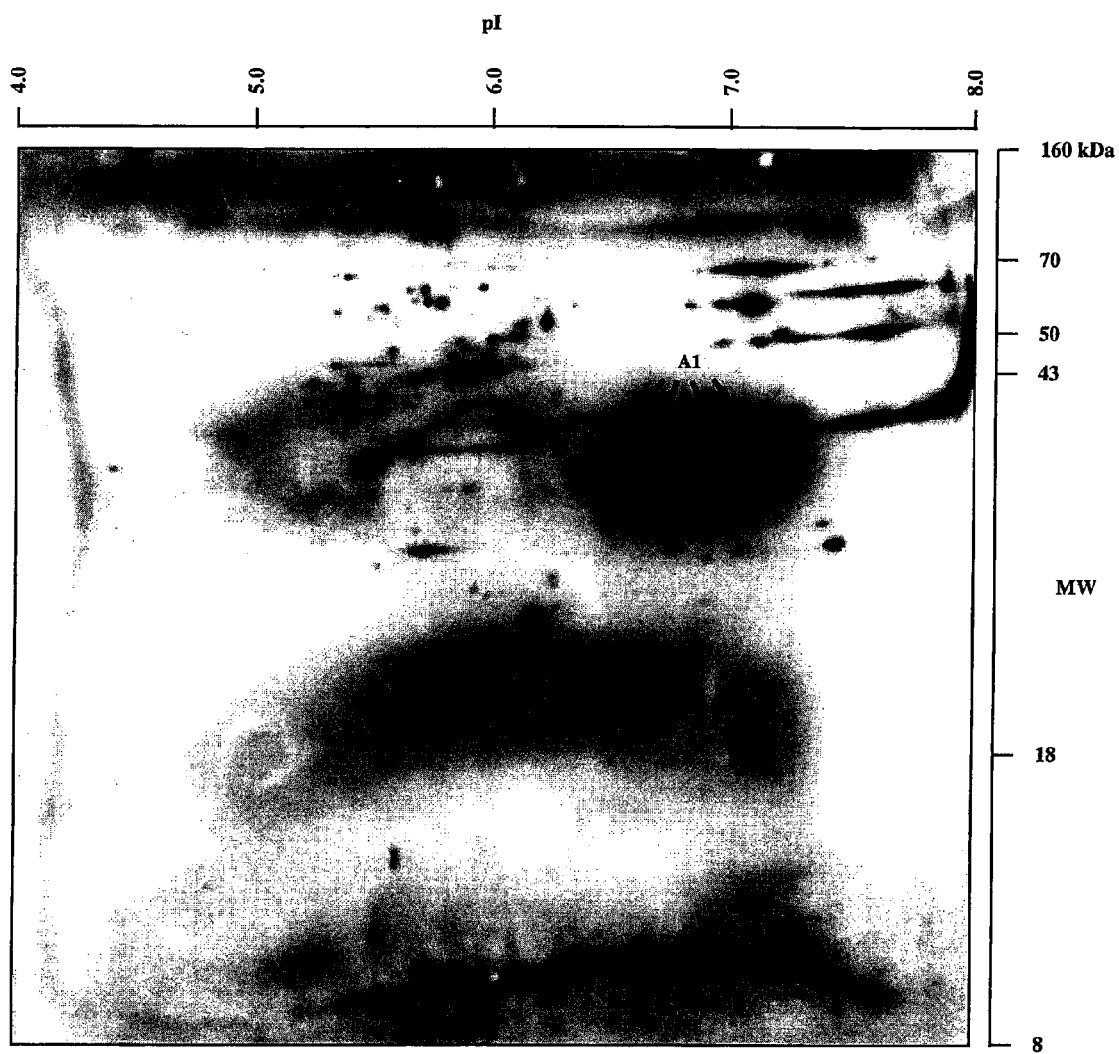

FIG. 2. Western blot of a two-dimensional gel separation of a A549 cell lysate treated with serum from a lung cancer patient. Reactivity was observed in a group of contiguous protein spots designated A1 with a pI of between 6.3 and 6.8 and a molecular weight of 37 kDa.

Figure 3:
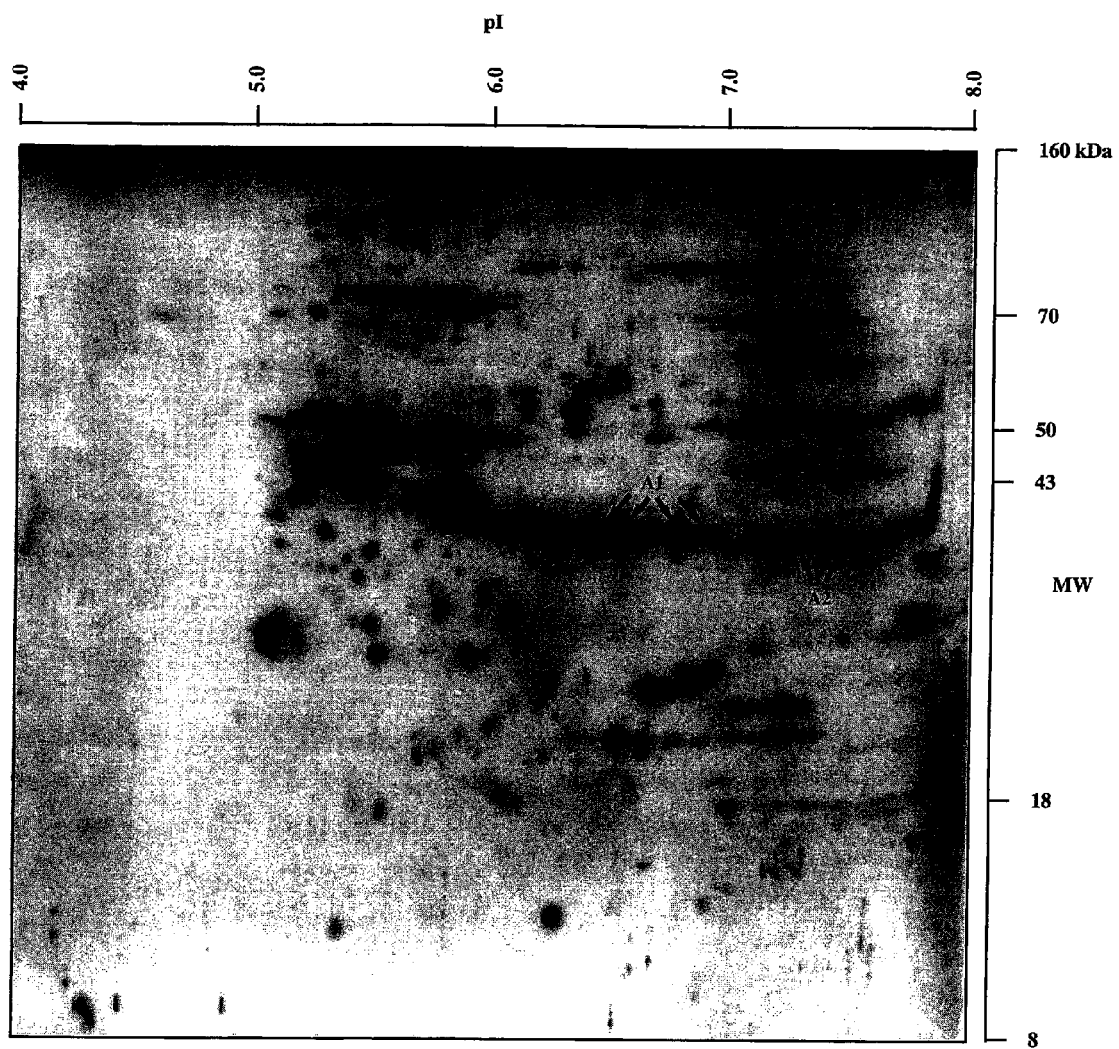
Figure 4B:
Figure 4A:
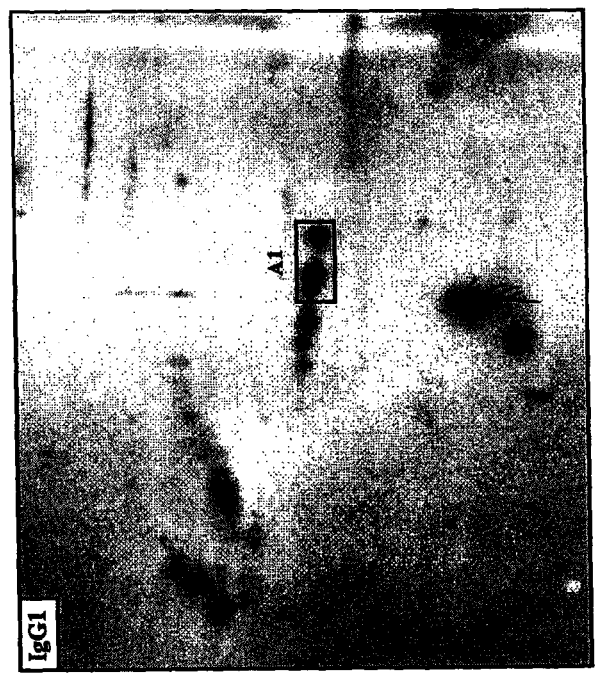
Figure 4D:
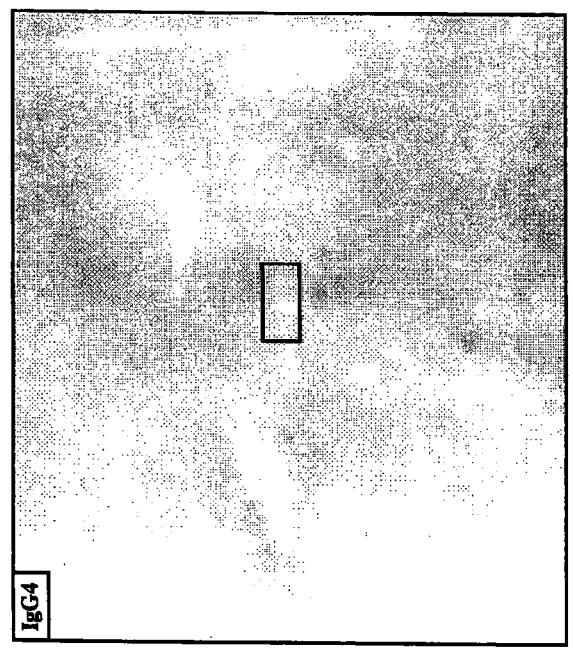
Figure 4C:
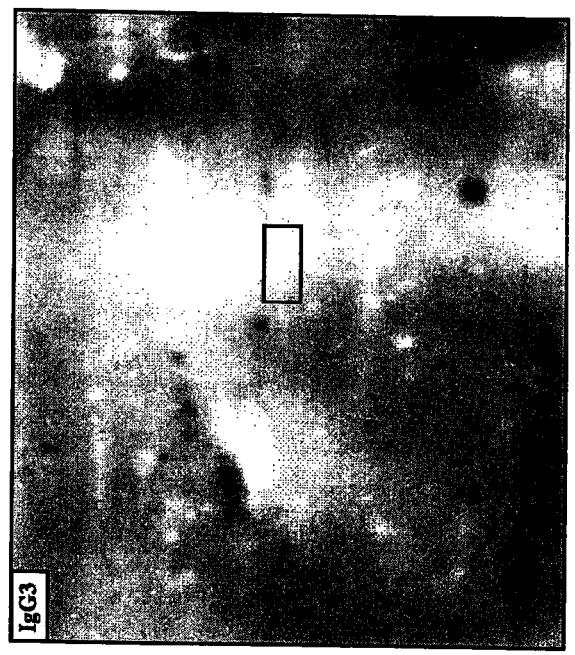
Figure 5B:
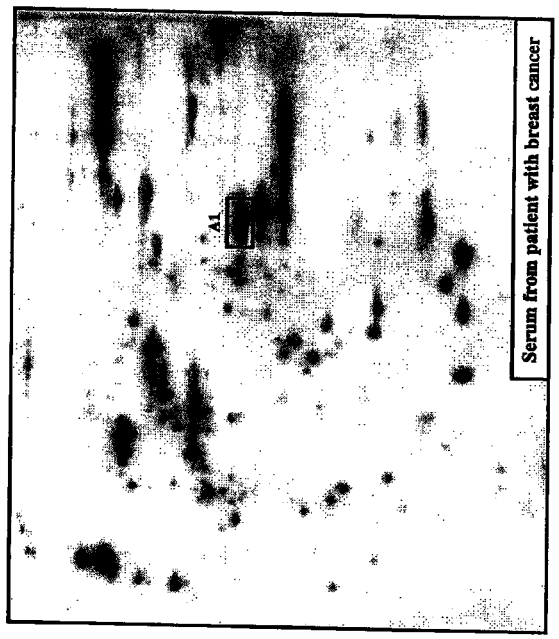
Figure 5A:
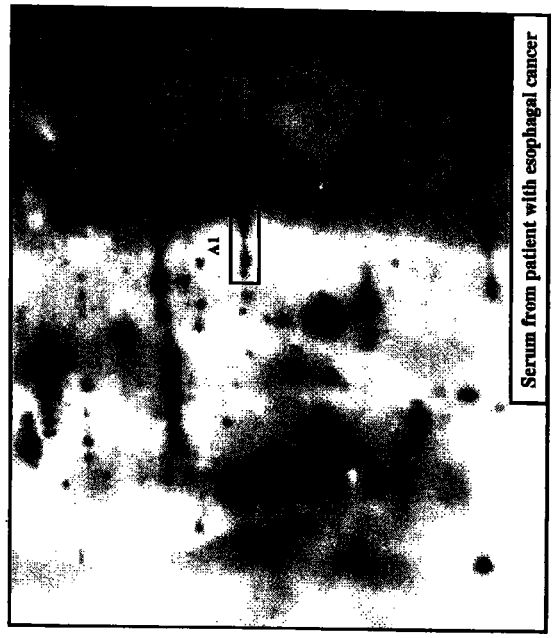
Figure 5D:
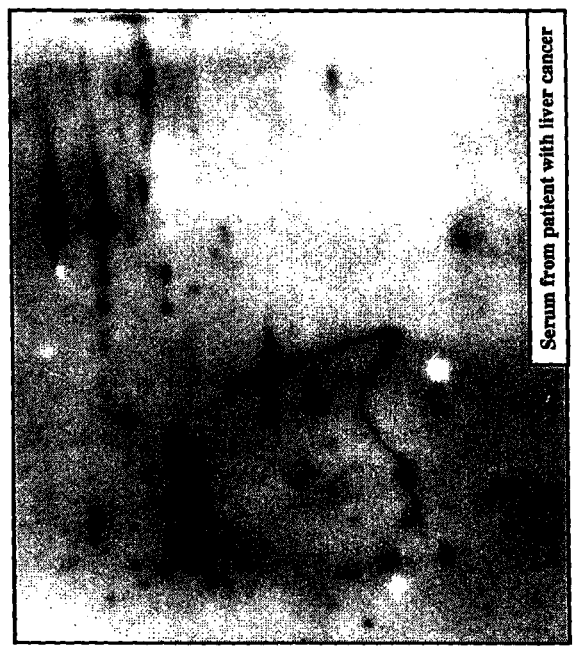
Figure 5C:
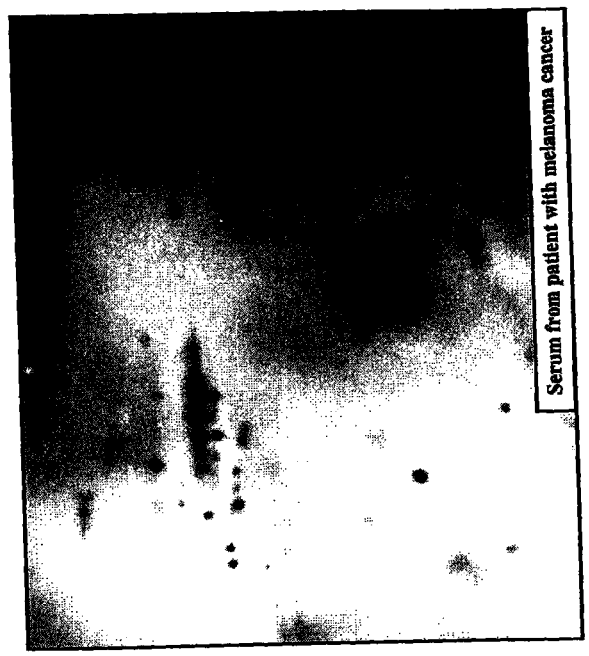

FIG. 3. IgM immunoreactivity against lung cancer proteins. Western blot of a two-dimensional gel separation of A549 lysates treated with serum from lung cancer patients. Membranes were subsequently incubated with a horseradish peroxidase-conjugated sheep anti-human IgM antibody.

FIGS. 4A-D. IgG subtype immunoreactivity against lung cancer patient sera. Western blots of a two-dimensional gel separation of A549 lysates with serum from lung cancer patients. Membranes were subsequently hybridized with horseradish peroxidase-conjugated mouse anti-human IgG1 (A), IgG2 (B), IgG3 (C) or IgG4 (D) antibody.

FIGS. 5A-D. Specificity of A1 and A2 IgG antibodies to lung cancer patient sera. Membranes containing A549 lysates were hybridized with sera from patients with melanoma, breast cancer, liver cancer or esophagal cancer. None of the sera exhibited IgG based immunoreactivity against A2. A1 proteins were observed with sera from patients with esophagal cancer (5/8) (A), breast cancer (1/11) (B), but were absent with sera from patients with melanoma, (0/7) (C) and liver cancer (0/11) (D).

Figure 6A:
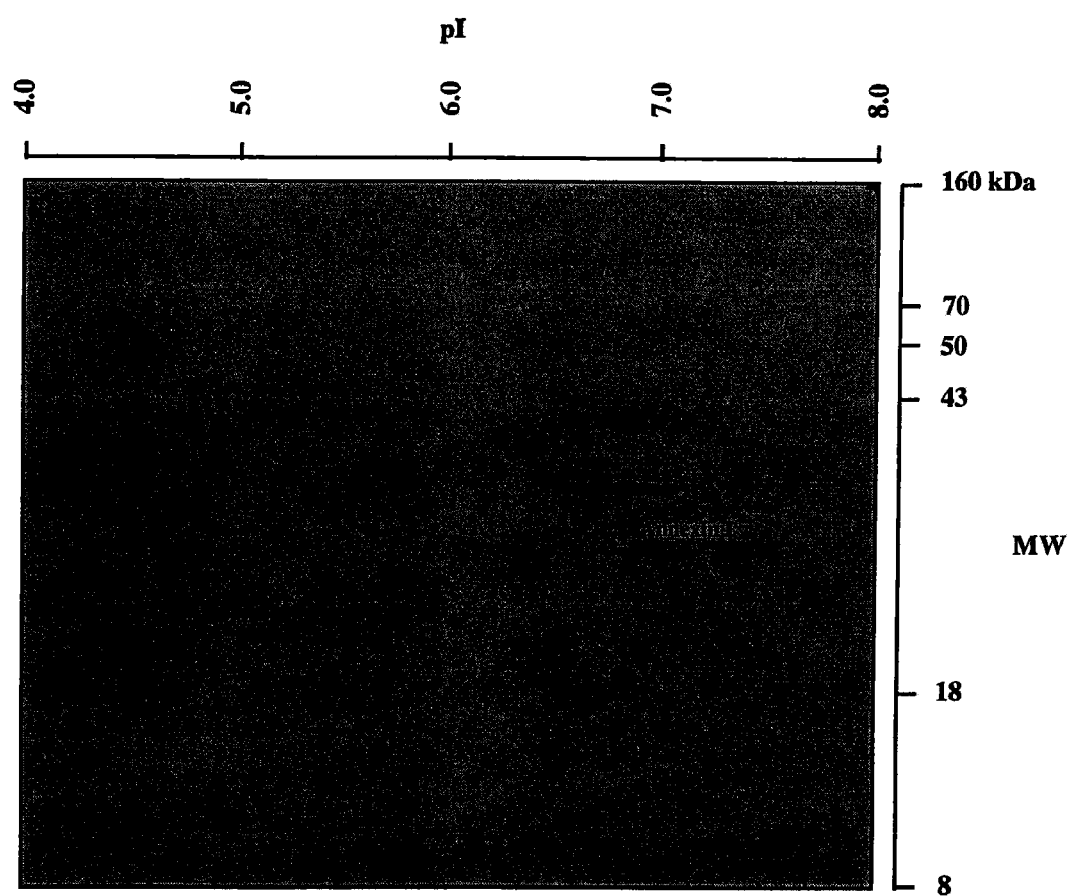

FIGS. 6A and B. Anti-Annexin I (A), and anti-Annexin II (B) antibodies are immunoreactive against proteins in the A1 and A2 spots respectively.

5. DETAILED DESCRIPTION OF THE INVENTION

The present invention achieves a highly desirable objective, namely providing methods for the diagnostic and prognostic evaluation of subjects with cancer and the identification of subjects exhibiting a predisposition to developing cancer. The assays of the invention comprise methods designed to detect increased levels of annexin protein production, or the presence of annexin autoantibodies, in serum or other biological samples from a subject. For purposes of the present invention, annexin proteins are characterized by a canonical motif in which a stretch of approximately 70 amino acids is repeated at least four times (Wallner, B. P. et al., 1986, Nature 320:77-80; Weber, K. and Johnson, N., 1986, FEBS Lett. 203: 95-98; Saris, C. J. M. et al., 1986, Cell 46:201-212; Huang K. S. et al., 1986, Cell 46:191-199).

Specifically, the invention encompasses a method for diagnosis and prognosis of cancer in a subject comprising:
(a) quantitatively detecting annexin protein in a biological sample derived from a subject; and
(b) comparing the level of protein detected in the subject's sample to the level of protein detected in a control sample, wherein an increase in the level of annexin protein detected in the subject's sample as compared to control samples is an indicator of a subject with cancer or at increased risk for cancer. In addition to detecting annexin protein, annexin derived peptides, antigens or differentially modified annexin proteins may be detected for diagnosis and/or prognosis of cancer.

A wide variety of protein mixtures that may contain annexin proteins can be prepared or assayed for the level of protein expression. In a preferred embodiment tumor tissue samples, including but not limited to lung tissue samples, derived from subjects suspected of, or predisposed to cancer can be used to screen for increased levels of annexin protein production.

The present invention encompasses a method for diagnosis and prognosis of a subject with cancer, comprising:
(a) contacting an antibody-containing biological sample derived from a subject, with a sample containing annexin protein antigens under conditions such that an immunospecific antigen-antibody binding reaction can occur; and
(b) detecting the presence of immunospecific binding of autoantibodies present in the subject's biological sample to the annexin protein, wherein the presence of immunospecific binding of autoantibodies indicates the presence of cancer in the subject.

In a specific embodiment of invention, annexin proteins, including but not limited to Annexin I and II and peptides derived therefrom, are purified and utilized to screen a subject's serum for the presence of circulating autoantibodies to such protein antigens, by means of sensitive and rapid immunoadsorbent assays or by other procedures.

The present invention also provides for kits for carrying out the above-described methods. The methods can be performed, for example, by utilizing pre-packaged diagnostic kits comprising at least a reagent for detecting annexin protein such as an anti-annexin antibody. Alternatively, the diagnostic kits comprise an annexin protein or antigenic protein fragment for detection of annexin autoantibodies in a subject derived sample.

The present invention is based on the discovery that levels of Annexin I and II proteins are increased in adenocarcinoma and squamous cell lung tumors derived from subjects with cancer. Additionally, increased levels of circulating autoantibodies reactive against annexin proteins have been detected in the serum of subjects having adenocarcinoma and squamous cell lung tumors.

5.1. Assays for Detection of Annexin Production

In accordance with the invention, measurement of levels of annexin proteins in samples derived from a subject can be used for the early diagnosis of diseases such as cancer. Moreover, the monitoring and quantitation of annexin protein levels can be used prognostically to stage the progression of the disease and to evaluate the efficacy of agents used to treat a cancer subject.

The detection of annexin proteins in a sample from a subject can be accomplished by any of a number of methods. Preferred diagnostic methods for the detection of annexin proteins in the biological sample of a subject can involve, for example, immunoassays wherein annexin proteins are detected by their interaction with an annexin specific antibody. Antibodies useful in the present invention can be used to quantitatively or qualitatively detect the presence of annexins or antigenic fragments thereof. In addition, reagents other than antibodies, such as, for example, polypeptides that bind specifically to annexin proteins can be used in assays to detect the level of annexin protein expression. Alternatively, detection of annexin proteins may be accomplished by detection and measurement of levels of biological properties associated with annexin proteins, such as for example, phopholipase A, and anticoagulant activity.

Immunoassays useful in the practice of the invention include but are not limited to assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, to name but a few.

A biological sample which may contain annexin proteins, such as lung tissue or other biological tissue, is obtained from a subject suspected of having a particular cancer or risk for cancer. Aliquots of whole tissues, or cells, are solubilized using any one of a variety of solubilization cocktails known to those skilled in the art. For example, tissue can be solubilized by addition of lysis buffer comprising (per liter) 8 M urea, 20 ml of Nonidet P-40 surfactant, 20 ml of ampholytes (pH 3.5-10), 20 ml of 2-mecaptoethanol, and 0.2 mM of phenylmethylsulfonyl fluoride (PMSF) in distilled deionized water.

Immunoassays for detecting expression of annexin protein typically comprise contacting the biological sample, such as a tissue sample derived from a subject, with an anti-annexin antibody under conditions such that an immunospecific antigen-antibody binding reaction can occur, and detecting or measuring the amount of any immunospecific binding by the antibody. In a specific aspect, such binding of antibody, for example, can be used to detect the presence and increased production of annexin proteins wherein the detection of increased production of annexin proteins is an indication of a diseased condition. The levels of annexin protein in a biological sample are compared to norms established for age and gender-matched normal individuals and for subjects with a variety of non-cancerous or pre-cancerous disease states.

In an embodiment of the invention, the biological sample, such as a tissue extract is brought in contact with a solid phase support or carrier, such as nitrocellulose, for the purpose of immobilizing any proteins present in the sample. The support is then washed with suitable buffers followed by treatment with detectably labeled annexin specific antibody. The solid phase support is then washed with the buffer a second time to remove unbound antibody. The amount of bound antibody on the solid support is then determined according to well known methods. Those skilled in the art will be able to determine optional assay conditions for each determination by employing routine experimentation.

One of the ways in which annexin antibodies can be detectably labeled is by linking the antibody to an enzyme, such as for use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.; Voller, A., et al., 1978, J. Clin. Pathol. 31:507-520; Butler, J. E., 1981, Meth. Enzymol. 73:482-523). The enzyme which is bound to the antibody will react with an appropriate substrate, preferably a chromogenic substrate, in such a manner as to produce a chemical moiety that can be detected, for example, by spectrophotometric, fluorimetric, or by visual means. Enzymes that can be used to detectable label the antibody include, but are not limited to, horseradish peroxidase and alkaline phosphatase. Detection can also be accomplished by colorimetric methods that employ a chromogenic substrate for the enzyme.

Detection of annexin antibodies may also be accomplished using a variety of other methods. For example, by radioactively labeling the antibodies or antibody fragments, it is possible to detect annexin protein expression through the use of a radioimmunoassay (RIA) (see, for example, Weintraub, B., Principles of Radioimmunoassays, Seventh Training Course on Radioligand Assay Techniques, The Endocrine Society, March 1986). The radioactive isotope can be detected by such means as the use of a gamma counter or a scintillation counter or by autoradiography.

The antibody may also be labeled with a fluorescent compound. Among the most commonly used fluorescent labeling compounds are fluorescein isothiocyanate, rhodamine, phycoerythrin and fluorescamine. Likewise, a bioluminescent compound may be used to label the annexin antibody. The presence of a bioluminescence protein is determined by detecting the presence of luminescence. Important bioluminescence compounds for purposes of labeling are luciferin, luciferase and aequorin.

In a specific embodiment of the invention, the levels of annexin proteins in biological samples can be analyzed by two-dimensional gel electrophoresis. Methods of two-dimensional electrophoresis are known to those skilled in the art. Biological samples, such as tissue samples, are loaded onto electrophoretic gels for isoelectric focusing separation in the first dimension which separates proteins based on charge. A number of first-dimension gel preparations may be utilized including tube gels for carrier ampholytes-based separations or gels strips for immobilized gradients based separations. After first-dimension separation, proteins are transferred onto the second dimension gel, following an equilibration procedure and separated using SDS PAGE which separates the proteins based on molecular weight. When comparing biological samples derived from different subjects, multiple gels are prepared from individual biological samples (including samples from normal controls).

Following separation, the proteins are transferred from the two-dimensional gels onto membranes commonly used for Western blotting. The techniques of Western blotting and subsequent visualization of proteins are also well known in the art (Sambrook et al, "Molecular Cloning, A Laboratory Manual", $2^{nd}$ Edition, Volume 3, 1989, Cold Spring Harbor). The standard procedures may be used, or the procedures may be modified as known in the art for identification of proteins of particular types, such as highly basic or acidic, or lipid soluble, etc. (See for example, Ausubel, et al., 1999, Current Protocols in Molecular Biology, Wiley & Sons, Inc., N.Y.). Antibodies that bind to the annexin proteins are utilized in an incubation step, as in the procedure of Western blot analysis. A second antibody specific for the first antibody is utilized in the procedure of Western blot analysis to visualize proteins that reacted with the first antibody.

The detection of annexin protein levels in biological samples can also be used to monitor the efficacy of potential anti-cancer agents during treatment. For example, the level of annexin protein production can be determined before and during treatment. The efficacy of the agent can be followed by comparing annexin expression throughout the treatment. Agents exhibiting efficacy are those which decrease the level of annexin protein production as treatment with the agent progresses.

The present invention is demonstrated by way of example wherein elevated levels of annexin proteins have been detected in tissue samples derived from patients with lung adenocarcinoma and squamous cell lung carcinoma. In particular, increased levels of Annexin I and II were detected in samples derived from lung cancer patients. The detection and/or quantitative measurement of annexin proteins in biological samples can be used in screening of subjects who are at risk for developing certain types of cancers or other proliferative disorders in which the annexin proteins are overexpressed. In addition, qualitative differences in the pattern of occurrence in serum or biological fluids of different members of the annexin family of proteins can be used as a screening, diagnostic or prognostic indicator of cancer or cancer risk.

5.2. Assays for Detection of Anti-Annexin Autoantibodies

The present invention provides diagnostic and prognostic methods for diseases such as cancer based on detection of circulating annexin autoantibodies in a subject. The method is validated by the use of a biological sample from a subject with cancer and from age and gender matched controls, without cancer. A biological sample which may contain autoantibodies, such as serum, is obtained from a subject suspected of having a particular cancer or suspected of being predisposed to developing cancer. A similar body fluid is obtained from a control subject that does not have cancer.

In accordance with the invention, measurement of autoantibodies reactive against the annexin protein antigens can be used for the early diagnosis of diseases such as cancer. Moreover, the monitoring of autoantibody levels can be used prognostically to stage the progression of the disease. The detection of autoantibodies in a serum sample from a patient can be accomplished by any of a number of methods. Such methods include immunoassays which include, but are not limited to, assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, to name but a few.

Such an immunoassay is carried out by a method comprising contacting a serum sample derived from a subject with a sample containing the annexin protein antigens under conditions such that an immunospecific antigen-antibody binding reaction can occur, and detecting or measuring the amount of any immunospecific binding by the autoantibody. In a specific aspect, such binding of autoantibody by tissue sections, for example, can be used to detect the presence of autoantibody wherein the detection of autoantibody is an indication of a diseased condition. The levels of autoantibodies in a serum sample are compared to the levels present in an analogous serum sample from a subject not having the disorder.

The immunoassays can be conducted in a variety of ways. For example, one method to conduct such assays involves anchoring of annexin protein onto a solid support and detecting anti-annexin antibodies specifically bound thereto. The annexin proteins to be utilized in the assays of the invention can be prepared via recombinant DNA techniques well known in the art. For example, a DNA molecule encoding an annexin protein or an antigenic fragment thereof can be genetically engineered into an appropriate expression vector for large scale preparation of annexin protein. It may be advantageous to engineer fusion proteins that can facilitate labeling, immobilization or detection of the annexin protein. See, for example, the techniques described in Sambrook et al., 1989, Molecular Cloning: A laboratory Manual, Cold Spring Harbor Press, Cold Spring Harbor, N.Y. Alternatively, the annexin protein may be purified from natural sources, e.g., purified from cells, using protein separation techniques well known in the art. Such purification techniques may include, but are not limited to molecular sieve chromatography and/or ion exchange chromatography. In practice, microtitre plates are conveniently utilized as the solid support for the annexin proteins. The surfaces may be prepared in advance and stored.

The present invention is demonstrated by way of example wherein elevated levels of circulating autoantibodies reactive against several annexin protein antigens have been detected in the sera of cancer patients. The detection and/or quantitative measurement of circulating anti-annexin autoantibodies in serum can be used in screening of subjects who are at risk for cancer or other proliferative disorders in which annexin protein levels are increased.

5.3. Immunotherapy

The invention also relates to the use of annexin proteins as antigens to immunize patients suffering from diseases characterized by the production of the annexin protein antigens. Stimulation of an immunological response to such antigens, is intended to elicit a more effective attack on tumor cells; such as inter alia inhibiting tumor cell growth or facilitating the killing of tumor cells. The identification of autoantibodies to annexin protein antigens associated with particular cancers provides a basis for immunotherapy of the disease.

The patient may be immunized with the annexin protein antigens to elicit an immune response which facilitates killing of tumor cells or inhibiting tumor cell growth. The annexin protein antigens can be prepared using the methods described above for purification of proteins.

In an embodiment of the invention an immunogen comprising a purified annexin protein antigen to which a patient with cancer has developed autoantibodies, is used to elicit an immune response. For administration, the annexin protein antigen should be formulated with a suitable adjuvant in order to enhance the immunological response to the protein antigen. Suitable adjuvants include, but are not limited to mineral gels, e.g. aluminum hydroxide, surface active substances such as lysolecithin, pluronic polyols, polyanions, peptides, oil emulsions, and potentially useful human adjuvants such as BCG (bacilli Calmett-Guerin) and (*Corynebacterium parvum*). Many methods may be used to introduce the formulations derived above; including but not limited to oral, intradermal, intramuscular, intraperitoneal, intravenous, and subcutaneous.

5.4. Kits

The present invention further provides for kits for carrying out the above-described assays. The assays described herein can be performed, for example, by utilizing pre-packaged diagnostic kits, comprising at least an annexin peptide (for detection of Annexin autoantibodies) or an annexin antibody reagent (for detection of annexin protein), which can be conveniently used, e.g., in clinical settings to diagnose disorders such as cancer.

In a first series of nonlimiting embodiments, a kit according to the invention comprises components for detecting and/or measuring human IgG antibodies directed toward annexin antigen. As one example, where the antibodies are detected and/or measured by enzyme linked immunoabsorbent assay (ELISA), such components may comprise target antigen, in the form of at least one and preferably a plurality of different annexin antigens or epitopes thereof, linked to a solid phase, and a means for detecting a human antibody bound to target antigen. Such means for detection may be, for example, an antibody directed toward the constant region of human IgG (e.g., rabbit anti-human IgG antibody), which may itself be detectably labeled (e.g., with a radioactive, fluorescent, calorimetric or enzyme label), or which may be detected by a labeled secondary antibody (e.g., goat anti-rabbit antibody).

In a second series of nonlimiting embodiments, a kit according to the invention may comprise components which detect and/or measure annexin antigens in the biological sample of a subject. For example, where annexin proteins are detected and/or measured by enzyme linked immunoabsorbent assay (ELISA), such components may comprise an antibody directed to epitopes of the annexin proteins which can be used to detect and/or quantitate the level of annexin expression in the biological sample. The antibody itself may be detectably labeled with a radioactive, flourescent, colorimetric or enzyme label. Alternatively, the kit may contain a labeled secondary antibody.

6. EXAMPLE

Detection of Autoantibodies Specific for Annexin Proteins and Increased Levels of Annexin Protein Expresseion in Cancer Patient Derived Samples Using the methods of the present invention, sera obtained from subjects with cancer were screened for reactivity against annexin proteins. The sera samples from cancer subjects were found to be reactive against annexin proteins. In addition, increased levels of annexin protein production were observed in tissue samples derived from subjects with cancer.

6.1. Materials and Methods

6.1.1. Reagents

All cell culture reagents, including Dulbecco's modified Eagle's medium (DMEM, containing L-glutamine, sodium pyruvate and pyridoxine hydrochloride), Dulbecco's phosphate buffered saline (PBS), fetal calf serum and penicillin/streptomycin were obtained from GIBCO-BRL (Grand Island, N.Y.). Mouse monoclonal anti-Annexin I and II antibodies were obtained from ICN (Costa Mesa, Calif.). Mouse monoclonal anti-human IgM antibody was purchased from Sigma Chemical Company (St. Louis, Mo.). Horseradish peroxidase-conjugated mice anti-human IgG1, IgG2, IgG3 and IgG4 antibodies were purchased from Zymed Company (San Francisco, Calif.). Horseradish peroxidase-conjugated sheep anti-human IgG and the anti-mouse IgG monoclonal antibodies, the ECL (Enhanced Chemiluminescence) kit and the Hyperfilm MP were obtained from Amersham (Arlington Heights, Ill.). Immobilon-P PVDF (polyvinylidene fluoride) membranes were purchased from Millipore Corp. (Bedford, Mass.). The acrylamide used in the first dimension electrophoresis, urea, ammonium persulfate and PDA (piperazine diacrylamide) were all purchased from Bio-Rad (Rockville Center, N.Y.). The acrylamide used in the second dimension electrophoresis was purchased from Serva (Crescent Chemical, Hauppauge, N.Y.) and the carrier ampholytes (pH 4 to 8) and NP-40 were both purchased from Gallard/Schlessinger (Carle Place, N.Y.). All other reagents and chemicals were obtained from either Fisher or Sigma and were of the highest purity available.

6.1.2. Cell Culture and Preparation of Extracts

A549 human adenocarcinoma cell lines were cultured at 37° C. in a 6% $CO_2$-humidified incubator in DMEM supplemented with 10% fetal calf serum, 100 U/ml penicillin and 100 U/ml streptomycin. The cells were passaged weekly after they had reached 70-80% confluence.

Fresh tumor tissue was obtained at the time of diagnosis (i.e., biopsy tissue) from patients with lung cancer. The experimental protocol was approved by the University of Michigan Institutional Review Board for Approved Research Involving Human Subjects. Informed consent was obtained from the patients (or their families) prior to the study. Following excision, the tumor tissue was immediately frozen at −80° C., after which small amounts of tumor tissue were solublized in solubilization buffer and stored at −80° C. until use. Cultured cells were lysed by addition of 200 µl of solubilization buffer comprising of 8 M urea, 2% NP-40, 2% carrier ampholytes (pH 4 to 8), 2% β-mecaptoethanol and 10 mM PMSF, and harvested using a cell scraper. After an additional 100 µl of solubilization buffer was added, the solution containing the cell extracts was transferred into microfuge tubes and stored at −80° C. until use.

6.1.3. 2-D Page and Western Blotting

Proteins derived from the extracts of both cultured cells or solid tumors were separated in dimensions as previously described (Strahler et al., 1989, Two-dimensional polyacrylamide gel electrophoresis of proteins. In "Protein Structure: A Practical Approach" T. E. Creighton (ed.) IRL Press, Oxford, U.K., pp 65-92), with some modifications. Briefly, subsequent to cellular lysis in solubilization buffer, 35 µl aliquots of solubilized tumor tissue or cultured cells derived from approximately $2.5 \times 10^6$ cells were applied onto isofocusing gels. Isoelectric focusing was conducted using pH 4 to 8 carrier ampholytes at 700 V for 16 h, followed by 1000 V for an additional 2 h. The first-dimension tube gel was loaded onto a cassette containing the second dimension gel, after equilibration in second-dimension sample buffer (125 mM Tris (pH 6.8), containing 10% glycerol, 2% SDS, 1% dithiothreitol and bromophenol blue). For the second-dimension separation, an acrylamide gradient of 11% to 14% was used, and the samples were electrophoresed until the dye front reached the opposite end of the gel. The separated proteins were transferred to an lmmobilon-P PVDF membrane. Protein patterns in some gels were visualized by silver staining, and on some lmmobilon-P membranes by coomassie blue-staining of the membranes. Unstained membranes prepared for hybridization were incubated with blocking buffer (comprising Tris buffered saline (TBS) containing 1.8% nonfat dry milk and 0.1% Tween 20) for 2 h, then washed and incubated with serum obtained either from patients, or with normal control serum (300 µl of serum, at a 1:100 dilution) for 1 h at room temp. Following three washes with blocking buffer, the membranes were incubated with a horseradish peroxidase-conjugated sheep anti-human IgG antibody (at a 1:1000 dilution) for 30 min at room temp. The membranes were washed 5 times with TBS containing 0.1% Tween 20, once in TBS, briefly incubated in ECL and exposed to hyperfilm™ MP for 10-30 min. Patterns visualized after hybridization with patients sera were compared directly to both the coomassie blue-stained blots from the same sample to determine correlation with proteins, as well as to patterns obtained from hybridization of blots derived from the same sample with sera from patients with other solid tumors or control sera to determine the specificity of autoantigens. Alternatively membranes were incubated with a horseradish peroxidase-conjugated sheep anti-human IgM antibody and processed as for incubations with anti-human IgG antibody.

Protein spots in both tumor and lysates of lung adenocarcinoma cell lines that were visualized with patient sera, but not with control sera, were characterized further. A549 cell lysates were subjected to 2-D PAGE, after which the separated proteins were transferred to Immobilon-P membranes and subsequently stained with coomassie blue. Protein spots of interest were excised from the membrane and subjected to N-terminal amino acid sequencing and mass spectrometric analysis. The resultant sequences and peptide masses were utilized for database searches for protein identification.

6.1.4. Annexin I and II Detection by Immunoblotting

Two anti-Annexin I and II monoclonal antibodies were utilized. These primary antibodies were used at a 1:5000 dilution in immunoblotting assays and processed as for incubations with patient sera.

6.2. Results

6.2.1. Reactivity of Sera from Lung Cancer Patients with a Lung Cancer Protein Detected by Western Blot Analysis A549 cell proteins were separated by 2-D PAGE and transferred onto Immobilon-P PVDF membranes. For Western blot analysis, each membrane was treated with one serum sample. The samples included sera obtained at the time of diagnosis from 18 patients with lung adenocarcinoma, 11 patients with squamous cell lung carcinoma, 4 with small cell lung carcinoma, 2 with large cell lung carcinoma, 19 with unclassified lung cancer; 37 patients with other cancers (11 breast, 7 melanoma, 11 liver, and 8 esophageal cancer; and from 15 healthy subjects without a prior history of cancer or autoimmune disease.

An example of a 2-D gel of A549 cells stained with silver is shown in FIG. 1. Hybridization of membranes using patient sera as the primary antibody and sheep anti-human IgG as secondary antibody revealed variable patterns of reactivity among patient sera with lung cancer. Duplicate hybridizations resulted in similar patterns. In general, several reactive spots were observed with most sera. Some of the reactive spots were observed with control sera and thus were considered to represent non-specific reactivity. Others were restricted to patient sera with lung cancer. Most noticeable among the latter was intense reactivity in a group of contiguous protein spots designated A1, with a pI between 6.3 and 6.8 M.W. of 37 kDa (FIG. 2), which was observed with sera of 8 of 18 lung adenocarcinoma patients, 4 of 11 squamous cell lung carcinoma patients, 1 of 4 small cell lung carcinoma, and 2 of 19 unclassified lung cancer patients and which was absent in A549 membranes hybridized with sera from normal individuals. A second group of contiguous protein spots designated A2 (FIG. 3), with a pI between 7.2 and 7.8 and MW of approximately 36 kDa was observed with sera of 7 of 18 lung adenocarcinoma patients, 3 of 11 squamous cell lung carcinoma patients, 2 of 4 small cell lung carcinoma patients, and 6 of 19 unclassified lung cancer patients but absent in sera from normal individuals. In total, 11 of 18 sera from patients with lung adenocarcinoma and 6 of 1 sera from patients with squamous cell lung carcinoma and 3 of 4 with small cell lung carcinoma exhibited reactivity for A1 and/or A2.

6.2.2. IgM Immunoreactivity Against Lung Cancer Proteins

To determine whether sera that exhibited IgG based immunoreactivity against A1 and/or A2 proteins also exhibited IgM based immunoreactivity, serum from three patients with lung adenocarcinoma that exhibited IgG based immunoreactivity against A1 and/or A2 and from two negative controls were included in this analysis. Membranes containing A549 lysates were hybridized with patient and control sera and subsequently incubated with a horseradish peroxidase-conjugated sheep anti-human IgM antibody. Only the patient serum that exhibited IgG based reactivity against A1 and A2 exhibited IgM based reactivity against these two contiguous set proteins (FIG. 3).

6.2.3. IgG Subtypes Immunoreactivity against Lung Cancer Proteins

To determine sera IgG subtype that exhibited IgG based immunoreactivity against A1 and/or A2 proteins, serum from three patients with lung adenocarcinoma that exhibited IgG immunoreactivity against A1 and/or A2 proteins and from two negative controls were included in this analysis. Membranes containing A549 lysates were hybridized with patient and control sera and subsequently incubated with a horseradish peroxidase-conjugated mouse anti-human IgG1, IgG2, IgG3 or IgG4 antibody. Only the patient sera that exhibited IgG based reactivity against A1 and/or A2 exhibited IgG1 based reactivity against these two contiguous sets of proteins (FIG. 4).

6.2.4. Specificity of A1 and A2 IgG Antibodies to Lung Cancer

Membranes containing A549 lysates were hybridized with sera from patients with melanoma, breast cancer, liver cancer or esophageal cancer. None of the sera exhibited IgG based immunoreactivity against A2, and the A1 proteins with sera from patients with esophagal cancer (5/8) (FIG. 5), with sera from patients with breast cancer (1/11), but absent in sera from patients with melanoma (0/7) and liver cancer (0/11).

6.2.5. Reactivity or Lung Cancer Patient Sera with Annexin I and II Isoforms To determine the identity of the A1 and A2 proteins, additional membranes were prepared from A549 lung adenocarcinoma cell lysates and the proteins were visualized by Coomasie blue staining. The A1 and A2 spots were excised from the membranes, eluted and subjected to trypsin digestion. Peptide fragments were analyzed by Mass Spectrometry. Four contiguous sections, designated A1a, A1b (just to the left of A1a, i.e. more acidic), A1c (just to the left of A1b, i.e. more acidic) and A1d (just to the left of A1c, i.e. more acidic) were excised from the blots. These four areas comprised, in total, the entire A1 region which was immunoreactive. Mass Spectrometric analysis of peptides derived from these sections revealed that Annexin I and Annexin II variants were the predominant Annexin I isoforms present except section A1a which produced no result. For A2 proteins, two contiguous sections, designated A2a and A2b (just to the left of A1b, i.e. more acidic) were excised from the blots. Mass Spectrometric analysis of peptides derived from these sections revealed that Annexin II variant (A2a) and Annexin II variant (A2b) were the predominant Annexin II isoforms present Additionally, A1 and A2 spots excised from the membranes and subjected to direct N-terminal sequencing. Since annexins are N-terminally blocked by acetylation, no results were obtained.

6.2.6. Further Confirmation of the Annexin I and II Isoforms

Figure 6B:
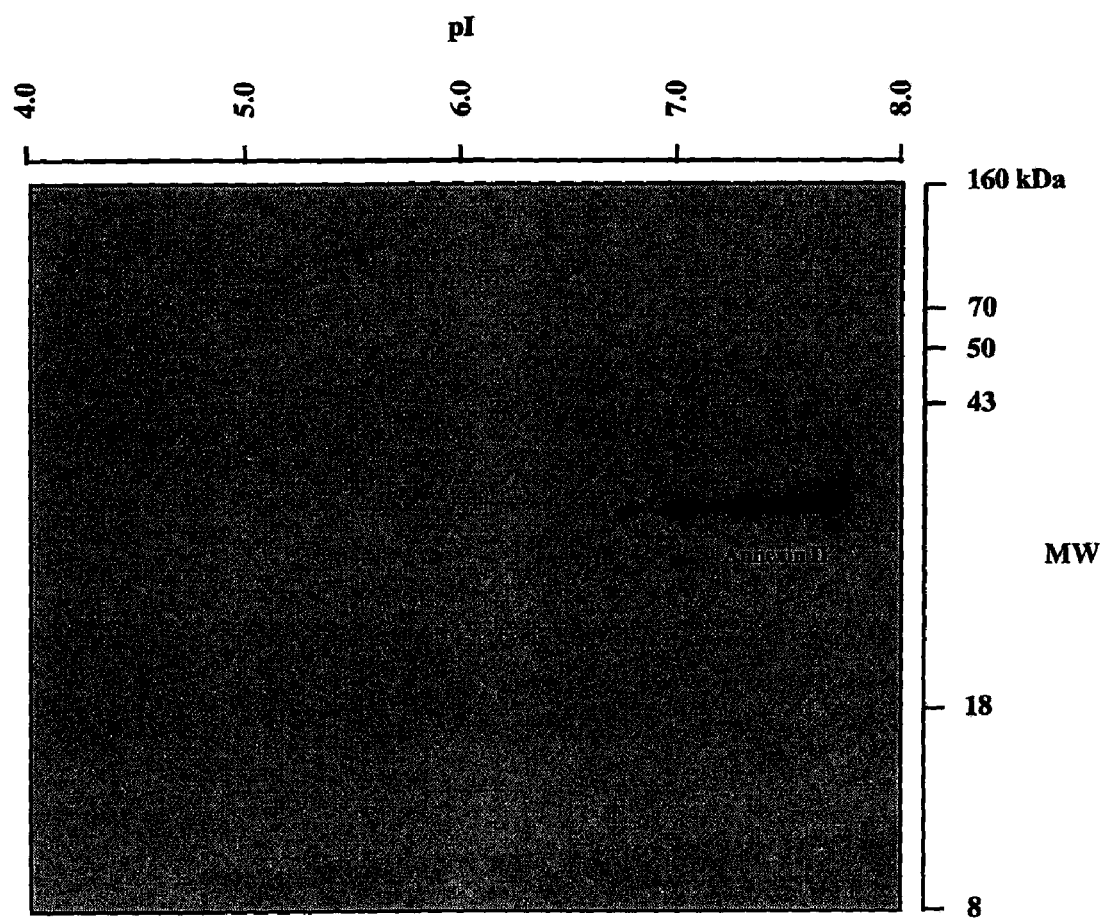

To confirm that spots A1 and A2 consisted of a mixture of Annexin I and Annexin II respectively, membranes prepared from both the A549 adenocarcinoma cell line were hybridized with either a commercially available mouse monoclonal antibody that reacts with Annexin I, or the mouse monoclonal Annexin II antibody. The immunoreactivity patterns obtained were compared to both coomassie blue-stained blots of the same cell lysate type as well as to the patterns of immunoreactivity observed with sera from patients with lung cancer. Anti-Annexin I, and anti-Annexin II antibodies immunoreacted with proteins in the A1 and A2 spots respectively visualized with lung cancer patient sera (FIG. 6). Strikingly, several additional low molecular weight immunoreactive spots were observed resulting from the hybridization of both monoclonal anti-Annexin I and II antibodies utilized. These spots have not shown immunoreactivity with any patient sera tested.

The present invention is not to be limited in scope by the embodiments disclosed in the examples which are intended as an illustration of one aspect of the invention, and any compositions or methods which are functionally equivalent are within the scope of this invention. Indeed, various modifications of the invention in addition to those shown and described herein will become apparent to those skilled in the art from the foregoing description. Such modifications are intended to fall within the scope of the claims.

We claim:

1. A method for diagnosis of lung cancer in a subject comprising:
   (a) quantitatively detecting levels of Annexin I and Annexin II proteins in a biological sample derived from a subject;
   (b) detecting levels of Annexin I and Annexin II proteins in a control sample; and
   (c) diagnosing the subject with lung cancer by comparing the levels of Annexin I and Annexin II proteins detected in the subject's sample to the levels of Annexin I and Annexin II proteins detected in the control sample, and identifying an increase in the levels of one or both of the Annexin I and Annexin II proteins in the subject's sample, wherein an increase in the level of one or both of the Annexin I and Annexin II proteins detected in the subject's sample as compared to a control sample is an indicator of a subject with lung cancer.

2. The method of claim 1 wherein the Annexin I and Annexin II proteins are detected using an immunoassay.

3. The method of claim 2 wherein the immunoassay is an immunoprecipitation assay.

4. The method of claim 1 wherein the sample is a lung tissue sample.

* * * * *